US012633410B2

(12) United States Patent
Neumann

(10) Patent No.: US 12,633,410 B2
(45) Date of Patent: May 19, 2026

(54) METHODS AND SYSTEMS FOR DETERMINING A PREDICTIVE INTERVENTION USING BIOMARKERS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 654 days.

(21) Appl. No.: 17/106,588

(22) Filed: Nov. 30, 2020

(65) Prior Publication Data

US 2022/0172836 A1 Jun. 2, 2022

(51) Int. Cl.
*G16H 50/20* (2018.01)
*G06N 20/00* (2019.01)

(52) U.S. Cl.
CPC ............. *G16H 50/20* (2018.01); *G06N 20/00* (2019.01)

(58) Field of Classification Search
None
See application file for complete search history.

(56) References Cited

U.S. PATENT DOCUMENTS

| | | | |
|---|---|---|---|
| 6,692,916 B2 | 2/2004 | Bevilacqua et al. | |
| 7,761,309 B2 | 7/2010 | Sacco et al. | |
| 7,853,626 B2 | 12/2010 | Jung et al. | |
| 7,953,613 B2 | 5/2011 | Gizewski | |
| 8,388,530 B2 | 3/2013 | Shusterman | |
| 9,492,114 B2 | 11/2016 | Reiman | |
| 10,085,643 B2 | 10/2018 | Bandic et al. | |
| 2011/0119212 A1* | 5/2011 | De Bruin ................. A61B 5/00 706/12 |
| 2011/0137851 A1* | 6/2011 | Cavet ................. G01N 33/6893 703/2 |
| 2011/0301977 A1* | 12/2011 | Belcher ................. G16H 40/63 715/764 |
| 2017/0159130 A1* | 6/2017 | Mitra .................... C12Q 1/6886 |
| 2017/0308981 A1* | 10/2017 | Razavian ............... G16H 40/60 |
| 2018/0068083 A1* | 3/2018 | Cohen .................... G16B 50/30 |
| 2018/0284141 A1 | 10/2018 | Ayton et al. | |

(Continued)

OTHER PUBLICATIONS

Berry et al. ("The Platform Trial: an Efficient Strategy for Evaluating Multiple Treatments." JAMA. 2015; 313(16):1619-1620) (Year: 2015).*

(Continued)

*Primary Examiner* — Christopher B Tokarczyk
(74) *Attorney, Agent, or Firm* — Caldwell LLC

(57) ABSTRACT

A system for determining a predictive intervention using biomarkers, the system including a computing device configured to receive physiological data from the subject, detect, using the physiological data, at least a biomarker linked to a malady, classify at least the biomarker to a plurality of intervention categories for the malady, wherein each intervention category of the plurality of intervention categories is a distinct classification of intervention based on physiological data, generate at least a combination of the plurality of intervention categories, assign efficacy values to the combination of the plurality of intervention categories as a function of addressing the malady, and provide, to the user, the combination as a function of the assigned values.

14 Claims, 7 Drawing Sheets

(56) References Cited

U.S. PATENT DOCUMENTS

2019/0027249 A1     1/2019  Fuksenko et al.
2021/0134451 A1*    5/2021  Fallen ................... G16H 10/60

OTHER PUBLICATIONS https://diginole.lib.fsu.edu/islandora/object/fsu%3A507684/datastream/
PDF/view; Analyzing Bone, Muscle and Adipose Tissue Biomark-
ers to Identify Osteosarcopenic Obesity Syndrome in Older Women;
by. Pegah Jafarinasabian.

* cited by examiner

METHODS AND SYSTEMS FOR DETERMINING A PREDICTIVE INTERVENTION USING BIOMARKERS

FIELD OF THE INVENTION

The present invention generally relates to the field of AI and simulation/modeling. In particular, the present invention is directed to determining a predictive intervention using biomarkers.

BACKGROUND

Chronic disorders have developed to reach epidemic proportions in many areas of the world and pose major risk factor for serious co-morbidities such as diabetes, cardio-vascular disease, dyslipidemia, neurodegenerative disease, and cancers.

SUMMARY OF THE DISCLOSURE

In an aspect, a system for determining a predictive intervention using biomarkers, the system including a computing device configured to receive physiological data from the subject, detect, using the physiological data, at least a biomarker linked to a malady, classify at least the biomarker to a plurality of intervention categories for the malady, wherein each intervention category of the plurality of intervention categories is a distinct classification of intervention based on physiological data, generate at least a combination of the plurality of intervention categories, assign efficacy values to the combination of the plurality of intervention categories as a function of addressing the malady, and provide, to the subject, the combination as a function of the assigned values.

In another aspect, a method for determining a predictive intervention using biomarkers, the method including receiving, by a computing device, physiological data from the subject, detecting, by the computing device, using the physiological data, at least a biomarker linked to a malady, classifying, by the computing device, at least the biomarker to a plurality of intervention categories for the malady, wherein each intervention category of the plurality of intervention categories is a distinct classification of intervention based on physiological data, generating, by the computing device, at least a combination of the plurality of intervention categories, assigning, by the computing device, efficacy values to the combination of the plurality of intervention categories as a function of addressing the malady, and providing, by the computing device, to the subject, the combination as a function of the assigned values.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining a predictive intervention using biomarkers. In an embodiment, the system includes a computing device configured to receive a physiological data from a subject and use a machine-learning process to generate a biomarker classifier to parse and classify physiological data. Computing device may calculate a figure of merit representing the match of the malady to the physiological data. Computing device is configured to classify the malady to a plurality of intervention categories. A plurality of intervention categories may be assigned values according to the efficacy of combining categories. The system may generate an objective function (a mathematical optimization function) that may be used by computing device to score each possible combination of predictive interventions. Numerical values may be determined by training a machine-learning model to derive numerical value.

Figure 1:
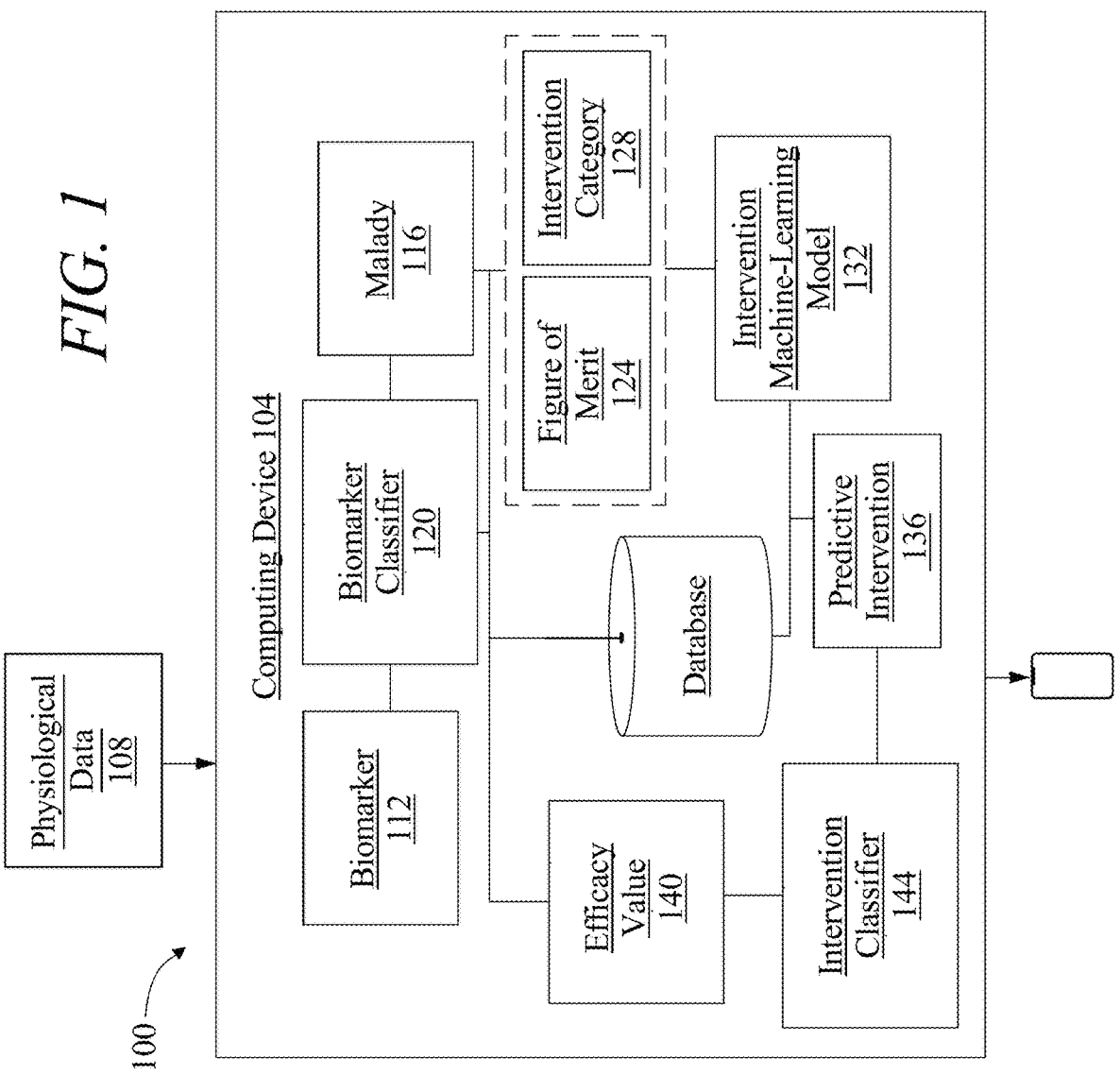
FIG. 1 is a block diagram illustrating an exemplary embodiment of a system for determining a predictive intervention using biomarkers.

Referring now to FIG. 1, an exemplary embodiment of a system 100 for determining a predictive intervention using biomarkers is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive physiological data from the subject. "Physiological data," as used in this disclosure, is chemical data, data originating from a biological extraction, medical data, and the like. Physiological data 108 may include biological extraction data such as blood panel, lipid panel, metabolic tests, microbiome assessment, genetic sequencing, and the like. Physiological data 108 may include genetic data including the presence of single nucleotide polymorphisms (SNPs), mutations, allele designations (dominant, recessive, +/−, etc.), genetic sequencing data, and the like; epigenetic data including methylation patterns, changes in gene expression patterns, enzyme concentrations, specific activity, circulating RNAs, and the like; microbiome data including gut microbiota, 'good' flora, transient flora, opportunistic pathogens, bacteria, viruses, parasites, fungi, circulating peptides, biologics, and the like; previous medical history including surgeries, treatments, prescriptions, current and past medications, allergies, family history of disease, diagnoses, prognoses, and the like; physiological data including systolic and diastolic blood pressure, resting heart rate, VO2 max, oxygen saturation, blood cell counts, hemoglobin/hematocrit levels, blood iron concentration, body mass index (BMI), blood sugar, HDL/LDL cholesterol levels, hormone levels, and the like; among any other data that one skilled in the art may recognize as physiological data 108 data that may be classified to a category, such as nutrition, endurance, strength, mental health, inflammation, disease, immunity, etc. Physiological data 108 may include a variety of data, from a variety of sources, with the data originating from the subject and/or a plurality of subjects, and from a variety of categories and sources, for instance and without limitation, as described in U.S. Nonprovisional application Ser. No. 16/886,647, filed on May 28, 2020, and entitled "METHODS AND SYSTEMS FOR DETERMINING A PLURALITY OF BIOLOGICAL OUTCOMES USING A PLURALITY OF DIMENSIONS OF PHYSIOLOGICAL DATA USER DATA AND ARTIFICIAL INTELLIGENCE," the entirety of which is incorporated herein by reference.

Continuing in reference to FIG. 1, computing device 104 is configured to identify a malady, as a function of the physiological data 108. Computing device 104 may detect, using the physiological data 108 data, at least a biomarker linked to a malady. A "biomarker," as used in this disclosure, is a datum of physiological data 108 data usable as a measurable indicator of the presence of and/or severity of a malady. Biomarker 112 may include any physiological data 108 datum classified to a malady. A "malady," as used in this disclosure, is an ailment, illness, disease, symptom, disorder, concern, or the like, diagnosed and/or undiagnosed in a subject. Malady 116 may include acute ailments, such as temporary soft-tissue injuries, viral infections, bacterial infections, dry skin, lack of sleep, and the like. Malady 116 may include diseases such as mental and cognitive disorders, long-term diagnoses, serious and terminal illnesses, and the like, which may or may not necessitate surgical intervention, pharmacological intervention, among other treatments. Malady 116 may include sports injuries, depression, diabetes, obesity, cancer, chronic sleep deprivation, high BMI, appetite control issues, substance abuse, and/or any other malady in a subject that may be detected from biomarkers 112 identified in physiological data 108 data.

Continuing in reference to FIG. 1, biomarker 112 may include, for instance and without limitation, physiological data 108 data relating to blood panel (blood test) data. Biomarker 112 may include red blood cell count (corpuscles). Red blood cells (RBC) are made in the bone marrow and broken down in the spleen and liver. RBC count may be elevated due to dehydration, high testosterone. RBC count may be low due to nutrient deficiencies (iron, vitamin B6, vitamin B12, folate), kidney dysfunction, chronic inflammation, anemia, blood loss, and the like. Biomarker 112 may include hemoglobin levels, which may be elevated due to dehydration, elevated testosterone, poor oxygen deliverability, thiamin deficiency, insulin resistance. Hemoglobin levels may be deceased due to anemia, liver disease, hypothyroidism, exercise, arginine deficiency, protein deficiency, inflammation nutrient deficiencies (vitamin E, magnesium, zinc, copper, selenium, vitamin B6, vitamin A). Biomarker 112 may include hematocrit levels which may be elevated due to dehydration, elevated testosterone, poor oxygen deliverability, thiamin deficiency, insulin resistance. Hematocrit levels may be deceased due to anemia, liver disease, hypothyroidism, exercise, arginine deficiency, protein deficiency, inflammation nutrient deficiencies (vitamin E, magnesium, zinc, copper, selenium, vitamin B6, vitamin A). Biomarker 112 may include mean corpuscular hemoglobin (MCH), or a measure of the average weight of hemoglobin per red blood cell. MCH may be elevated ("macrocytic") due to nutrient deficiencies (vitamin B12, folate, vitamin C), alcohol consumption, thiamin deficiency, and (falsely increased) by hyperlipidemia. MCH may be decreased ("microcytic") due to iron deficiency, nutrient deficiencies (vitamin B6, copper, zinc, vitamin A, vitamin C). Biomarker 112 may include measures of the average concentration of hemoglobin in red blood cells, which may be elevated ("macrocytic") due to nutrient deficiencies (vitamin B12, folate, vitamin C), alcohol consumption, thiamin deficiency, and (falsely increased) by hyperlipidemia. Concentration of hemoglobin may be decreased ("microcytic") due to iron deficiency, nutrient deficiencies (vitamin B6, copper, zinc, vitamin A, vitamin C). Biomarker 112 may include data on platelets or small, anucleated cell fragments in blood that are involved in clotting and important for vascular integrity. Platelets may be increased due to iron deficiency anemia, collagen diseases, hemolytic anemia, blood loss, stress, infection, inflammation. Platelets may be decreased due to alcoholism, liver dysfunction, viral/bacterial infections, pernicious anemia, bleeding. Biomarker 112 may include cellular dimension assessment, such as measures of the average size of platelets, reflecting their function. Platelets counts may be elevated due to increased platelet production, which is often caused by loss or destruction of existing platelets. Elevated mean platelet volume (MPV) may be associated with vascular disease and mortality, certain cancers, type 2 diabetes, and Hashimoto's thyroiditis. MPV may be decreased due to conditions associated with under-production of platelets such as aplastic anemia or cytotoxic drug therapy. Biomarker 112 may include red blood cell distribution width, a measurement of the variation in red blood cell size. Typically increased due to nutrient deficiency-related anemias (iron, vitamin A, copper, zinc, vitamin B6).

Continuing in reference to FIG. 1, biomarker 112 may include physiological data 108 data relating to immunological cells, immune system function, and the like. For instance and without limitation, biomarker 112 may include neutrophil levels, which may be elevated due to bacterial infection or inflammation. Neutrophil levels may be decreased due to nutrient deficiencies (copper, vitamin B12, folate), elevations in other white blood cells. Biomarker 112 may include lymphocyte levels including B-cells, T-cells, and Natural Killer Cells. Lymphocyte levels may be elevated due to viral infections, Crohn's, and other autoimmune diseases, hypoadrenalism. Lymphocyte levels may be decreased due to zinc deficiency, elevations in other white blood cells. Biomarker 112 may include data concerning white blood cells (WBC) that leave the circulation to become macrophages. WBC circulation data may be elevated due to inflammation, collagen disease (i.e. Rheumatoid Arthritis), ulcerative colitis, recovery after an infection or trauma. Biomarker 112 may include data concerning eosinophil immune cell activation in late stage inflammation. Immune cell activation may be elevated due to allergies, asthma, parasitic infection, hypoadrenalism, skin diseases such as eczema, ulcerative colitis, Crohn's, aspirin sensitivity. Immune cell activation may be decreased due to elevated cortisol, hormonal imbalance, certain cancers, medication side effects. Biomarker 112 may include data concerning basophil immune cell activation associated with inflammation and hypersensitivities, which may be elevated due to inflammation, allergies, hemolytic anemia, hypothyroidism.

Continuing in reference to FIG. 1, biomarker 112 may include physiological data 108 data relating to lipid biomarkers, for instance from a lipid panel. Biomarker 112 may include total cholesterol level, HDL level, LDL level, and the like. Biomarker 112 may include lipoprotein levels, a waxy, fat-protein macromolecular substance that travels throughout the body in carrier lipoproteins (HDL, LDL, and VLDL); a precursor to steroid hormones and bile salts. Lipoprotein profile may be elevated due to poor thyroid function, insulin resistance, blood glucose dysregulation, magnesium deficiency, dehydration, kidney disease, familial hypercholesterolemia, and may be decreased due to liver dysfunction, oxidative stress, inflammation, malabsorption, anemia. Biomarker 112 may include measures of blood levels of the major storage form of fat; also called triacylglycerols. Triacylglycerols may be related to determining fasting states in subjects; triacylglycerol profiles are implicated in cardiovascular disease. Triacylglycerols may be elevated due to blood glucose dysregulation, diabetes, hypercaloric diets, poor thyroid function, kidney disease, alcohol consumption, and may be decreased due to fat malabsorption, low carbohydrate diets, calorie restriction, potential autoimmunity. Biomarker 112 may include the amount of cholesterol associated with low density lipoprotein (LDL) particles in the blood. LDL may be elevated due to insulin resistance, blood glucose dysregulation, poor thyroid function, kidney disease, familial hypercholesterolemia, and may be decreased due to liver dysfunction, oxidative stress, malabsorption, anemia. Biomarker 112 may include the amount of cholesterol associated with high density lipoprotein (HDL) particles in the blood. HDL may be elevated due to inflammation, oxidative stress, excessive exercise. Decreased HDL is associated with metabolic syndrome and may be decreased due to insulin resistance, sedentary lifestyle, and/or poor diet.

Continuing in reference to FIG. 1, biomarker 112 may include metabolic data detected in physiological data 108 data, for instance from a comprehensive metabolic panel (CMP). Biomarker 1123 may include blood sugar concentration (glucose); may be elevated due to diabetes type 1 and 2, insulin resistance, increased stress hormones, or an inability to inhibit the liver's production of glucose, or (if not fasting) ingestion of a high carbohydrate meal. Biomarker 112 may include blood urea nitrogen (BUN), a marker of kidney function. BUN may be elevated due to dehydration, poor kidney function, high protein intake, fatty liver, catabolic stress. BUN may be decreased due to inadequate protein intake or protein malabsorption, liver disease, over hydration, and B6 deficiency. Biomarker 112 may include creatinine levels, a byproduct of creatine breakdown. Creatinine may be increased due to kidney disfunction, dehydration, excessive muscle breakdown or increased muscle mass, hyperthyroidism, high meat intake, ketones. Creatinine may be decreased due to poor musculature, poor protein intake or absorption. Biomarker 112 may include electrolyte (sodium, potassium, chloride) concentrations; sodium, a positively charged electrolyte, necessary for muscle contraction, nutrient absorption, neurological functioning, pH balance. Sodium may be elevated due to dehydration, hyperaldosterone (reabsorption of sodium), excess sodium intake. Sodium may be decreased due to elevated serum glucose, low cortisol, glycosuria, ketonuria, hypothyroidism, fluid loss through sweat; potassium, a positively charged electrolyte, necessary for muscle contraction, pH balance, nerve signal conduction, and action potentials. Potassium may be elevated due to renal failure, hypoaldosterone, acidosis, hemolysis, low insulin, hyperglycemia, exercise. Potassium may be decreased due to poor potassium intake, alkalosis, hyperaldosterone, excessive fluid loss, elevated insulin, low magnesium, elevated estrogen, increased catecholamines; chloride, a negatively charged electrolyte; important for maintaining cellular equilibrium across cell membranes and for the production of stomach acid. May be elevated due to kidney dysfunction, diarrhea, dehydration, hyperparathyroidism, hyperventilation. May be decreased due to vomiting, respiratory acidosis (hypoventilation), metabolic alkalosis, hypoaldosterone. Biomarker 112 may include measures of blood bicarbonate as a surrogate marker for $CO_2$ expiration and as a blood pH buffer. Blood bicarbonate may be elevated due to vomiting, metabolic alkalosis, respiratory acidosis (hypoventilation). Blood bicarbonate may be decreased due to metabolic acidosis, respiratory alkalosis (hyperventilation). Biomarker 112 may include uric acid, an end product of DNA purine base metabolism and excretion in the kidneys; uric acid may indicate oxidative stress and elevated levels are associated with cardiovascular disease and diabetes. Uric acid may be elevated due to gout, kidney dysfunction, excess alcohol intake, starvation, extreme calorie restriction, liver dysfunction, hemolytic anemia, excess fructose consumption, fungal infection, ketogenic diet, supplemental niacin, high protein diet, prolonged fasting, supplemental vitamin B3, excess acidity. Uric acid may be decreased due to nutrient deficiencies (molybdenum, zinc, iron), oxidative stress, low purine intake (vegetarian or vegan), excess alkalinity. Biomarker 112 may include a variety of metabolic data concerning the concentration and identities of albumin, globulin, calcium, phosphorous, alkaline phosphatase (ALP), alanine amino transferase (ALT/SGPT), aspartate amino transferase (AST/SGOT), LDH, bilirubin, GGT, iron, TIBC.

Continuing in reference to FIG. 1, biomarker 112 may include common, recommended biomarkers and/or disease-specific biomarkers such as C-Reactive Protein, cortisol, DHEA-Sulfate, estimated Glomerular Filtration Rate (eGFR), estradiol, ferritin, the body's iron binding protein. Such biomarkers may be elevated due to hemochromatosis and other genetic conditions, inflammation, liver damage, hemolytic or sideroblastic anemia, and may be decreased due to poor intake, poor absorption, chronic blood loss, chronic disease or infection, progesterone birth control pills. Biomarker 112 may include folate, hemoglobin A1c, homocysteine and other free amino acids, progesterone and other hormones, prostate Specific Ag (PSA), testosterone, Thyroid-Stimulating Hormone, vitamin D, 25-Hydroxy vitamin D. Biomarker 112 may include heavy metals and toxic compound concentrations such as arsenic, lead, cadmium, mercury, aluminum. Biomarker 112 may include antigens, both foreign and endogenous that may be indicative of malady 116. Persons skilled in the art, upon review of the disclosure in its entirety, will be aware of the various physiological data that may be collected about a subject, the biomarkers that may be present, and how machine-learning methods may become more robust with larger training data sets of physiological data 108 data for parsing, identifying, and classifying maladies and/or biomarkers 112.

Continuing in reference to FIG. 1, detecting at least the biomarker 112 may include generating a biomarker classifier using a classification machine-learning process to categorize physiological data to malady biomarkers. Classifying the physiological data 108 data to at least a biomarker category by generating a biomarker classifier, using a classification machine-learning process, may including training with training data that includes a plurality of data entries wherein each data entry models physiological data to malady biomarkers. A "biomarker category," as used in this disclosure is a classification of a biomarker 112. A "biomarker classifier," as used in this disclosure, is a classifier that is used for classifying physiological data 108 data to a classification of a malady. A "classifier," as used in this disclosure, is a machine learning model that combines a discovery component (algorithm that matches a physiological data datum to a biomarker category) with a learning component (such as performing supervised learning, reinforcement learning, unsupervised learning, etc.), as described in further detail below. A biomarker classifier 120 may identify biomarkers in physiological data 108. A biomarker category may include a qualitative identifier such as "blood panel test", or "elevated biomarkers", "decreased biomarker", "abnormal", "normal", "healthy", and the like. A biomarker category may include a quantitative datum such as "biomarker above X value", "biomarker below Y value," or the like, where the value is a threshold and/or limit that may be predetermined for sorting physiological data 108 into a biomarker 112 categorization that relates to a malady 116.

Continuing in reference to FIG. 1, training data for biomarker classifier 120 may include a plurality of data entries wherein each data entry models physiological data 108 data to malady biomarkers. A "malady biomarker," as used in this disclosure, is a malady-specific biomarker relationship. Malady biomarker may include specific single nucleotide polymorphisms (SNPs) (or set of SNPs) identified in genetic sequences, gene expression product isoforms, variants, concentrations, macromolecular post-translational modifications (methylation, phosphorylation, ubiquitination, etc.) enzyme specific activities, and the like, which relate to various disease states, disorders, and the like. For instance and without limitation, training data may include data that relates the presence of genetically-linked biomarkers in the fat4 gene, or the protocadherin FAT4 gene product family (CDHF14) tumor suppressor. Protocadherin Fat 4, also known as cadherin family member 14 (CDHF14) or FAT tumor suppressor homolog 4 (FAT4), is a protein that in humans is encoded by the FAT4 gene. FAT4 is associated with the Hippo signaling pathway. The Hippo pathway has emerged as a conserved signaling pathway that is essential for the proper regulation of organ growth in *Drosophila* and vertebrates, SNPs of which are associated with a variety of maladies, including cancer, obesity, weight management, effectiveness of weight loss therapeutics, and the like. Additionally, a second biomarker, the concentration of angiotensin I converting enzyme (ACE) before, after, and during a dietary period may be used as training data to further detail how a subject relates to weight loss, propensity to obesity, diabetes, and the like, for instance which may identify an intervention category of 'weight loss medication,' 'diet', and/or 'exercise'.

Continuing in reference to FIG. 1, training data, as used herein, may include physiological data 108. In a non-limiting illustrative example, training data may include gene expression levels, patterns, and epigenetic data including DNA methylation patterns, wherein training a machine-learning model (biomarker classifier 120) to identify relationships in the training data, that when presented with an input of physiological data 108 of a subject, the biomarker classifier 120 may categorize biomarkers 112 present to maladies 116 it may relate to. Training data may include data originating from the subject, for instance via a questionnaire and a user interface with computing device 104, wherein the subject may provide medical history data, upload genome sequencing data from a sequencing service, and the like. Training data may include data recorded and transmitted to computing device 104 via a wearable device such as a pedometer, gyrometer, accelerometer, motion tracking device, bioimpedance device, ECG/EKG/EEG data, physiological sensors, blood pressure monitor, blood sugar and VOC monitor, and the like, wherein wearable device may be in contact with subject, worn on the skin, within proximity of the subject, and the like. Training data may include data retrieved from online research repositories, such as National Institutes of Health (NIH), clinical trials, peer-reviewed scientific research, laboratory results, and the like. Training data may originate from any number of subjects, wherein the training data may become more robust with increasing datasets from a larger number of subjects. Training data may include data originating from an individual other than subject, including for instance an expert, physician, lab technician, nurse, caretaker, psychologist, therapist, and the like.

Continuing in reference to FIG. 1, detecting malady 116 may include indicating a figure of merit for a plurality of maladies as they correlate to at least the subject biomarker 112 and selecting the malady 116 based on the figure of merit. A "figure of merit," as used in this disclosure, is a quantity used to characterize the "fit" of a malady 116 for the biomarkers 112 detected in physiological data 108. A figure of merit 124 may include a numerical value, such as a percentile that indicates likelihood the malady fits a particular pattern of biomarkers. A figured of merit 124 may include a function of values that describe the performance of the biomarker classifier 120 for categorizing biomarkers 112 to maladies 116. A figure of merit 124 may include a qualitative determination such as a "fit" or "no fit", and/or a binary system of identification (such as a dichotomous key). A figure of merit 124 may include deciding a malady fit about a threshold, limit, or other value that computing device 104 may use to determine a "match" between physiological data 108 and malady 116. Computing device 104 may select malady 116 as a function of figured of merit 124 to determine intervention categories, for instance by selecting the malady 116 with a figure of merit 124 that indicates the highest likelihood malady 116 matches biomarkers 112. Computing device 104 may select malady 116 individually, regardless of figured of merit 124, by organizing maladies into a list, queue, and/or other organization based on the figured of merit 124. Figure of merit 124 may include any type of quantifier that informs system 100 on selecting a malady 116 from a subject's physiological data 108.

Continuing in reference to FIG. 1, computing device 104 may calculate figure of merit 124 using any mathematical expression and/or operation, such as addition, subtraction, multiplication, and the like. Computing device 104 may weight biomarker 112 by prevalence to malady 116. Computing device 104 may assign a score, or value, to biomarker 112 that relates to reliability of that biomarker 112, and use such a score to modify the 'weight' or 'prevalence' placed on that biomarker to calculate the figure of merit 124, for instance for generic biomarkers 112 that relate to a wide variety of diseases. Computing device may retrieve from an online research repository, peer-reviewed research articles, a database, or the like, using a web browser and the Internet to determine figure of merit 124 for each biomarker 112 to malady 116 relationship. Computing device 104 may use such data as training data for a machine-learning process, as described in further detail below, to generate figure of merit 124 for sets of biomarkers 112 as they relate to maladies 116.

Continuing in reference to FIG. 1, computing device 104 is configured to classify the malady 116 to a plurality of intervention categories for the malady, wherein each intervention category of the plurality of intervention categories is a distinct classification based on physiological data 108. An "intervention category," as used in this disclosure, is a classification of a subset of interventions (treatments, course-of-action, stand-of-treatment, guidance, advice, regimen, or the like), which may address malady 116. An intervention category 128 may include any number and/or type of category such as, for instance without limitation, 'dietary', 'nutritional,' 'fitness', 'sleep', 'medication', 'therapy', 'counseling', and the like. An intervention category 128 may include specific variables, numerical values, and the like, which distinguish subclassifications within category identifiers, for instance and without limitation, pharmacological drug classes within 'medication', dosages of the drugs, food types within 'diet', exercise recommendations within a 'fitness' category, and the like. Malady 116 may be classified to intervention category 128, for instance "diabetes" to "diet", wherein the diet category would have diets relating to subjects with diabetes. Biomarker 112 may then be classified to "diet" and/or "diet subtypes" as a function of diets that may match the biomarker 112, for instance "low sugar diets", wherein different variants of such a diet may include "eliminating lactose", "non-dairy", "plant-based", "vegan", etc. due to lactose intolerance identified from gene expression patterns lacking expression of the lactase enzyme, and microbiome data illustrating a lack of probiotics including *Lactobacillus* spp., and other homo- and heterofermentative probiotics.

Continuing in reference to FIG. 1, computing device 104 may identify and retrieve a plurality of intervention categories 128 relating to malady 116. Computing device 104 may, for instance and without limitation, identity intervention categories 128 using a web browser and the Internet, using a query search for mesh terms and/or identifiers associated with a malady 116. In non-limiting illustrative examples, computing device 104 may search an online research repository, such as PubMed (National Institutes of Health), clinical trial studies, peer-review scientific research, laboratory results, and the like, to identify intervention categories 128 associated with a malady 116. Computing device 104 may store and/or retrieve intervention categories 128 associated with a malady 116 in a database, for instance and without limitation, various diets and medications associated with malady 116, wherein each category may include a variety of diet types and class of drugs, dosages, regimen frequency, associated sex, age, bodyweight, and other physiological data 108 associated with the category. Computing device 104 may receive, store, and/or retrieve intervention categories 128 associated with subject. For instance, any current medications, dietary patterns, nutritional inputs (meals and food items consumed), fitness regimens (for instance form fitness tracking applications), and the like, to identify intervention categories 128.

Continuing in reference to FIG. 1, classifying the biomarker 112 to at least the intervention category 128 may include training an intervention machine-learning model, using a machine-learning process, with training data that includes a plurality of data entries wherein each data entry models intervention category 128 for the physiological data 108 to predictive interventions. An intervention machine-learning model 132 may include any machine-learning process, algorithm, and/or model, performed by computing device 104 using a machine-learning module, as described in further detail below. A "machine learning process," as used in this disclosure, is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a subject and written in a programming language.

Continuing in reference to FIG. 1, training data for intervention machine-learning model 132 may be the same training used for generating biomarker classifier 120. In non-limiting illustrative examples, training data may include blood protein and enzyme concentrations and specific activities for instance of fibrinogen, ferritin, serum amyloid A, α-1-acid glycoprotein, ceruloplasmin, hepcidin, haptoglobin, tumor necrosis factor-α (TNF-α), among other acute phase proteins; for instance cytokine identities and concentrations for instance interleukin-6 (IL-6); metabolites identities and concentrations such as blood sugar, LDL and HDL cholesterol content; hormone identities and concentrations such as insulin, androgens, cortisol, thyroid hormones, and the like; erythrocyte sedimentation rate, blood cell counts, plasma viscosity, and other biochemical, biophysical, and physiological properties regarding blood panels, blood tests, AST/ALT concentrations, and the like, for instance and without limitation as it relates to blood panel test, lipid panel test, hormone panel tests, and the like, performed by a physician. Training data for intervention machine-learning model 132 may include data retrieved from online research repositories, such as National Institutes of Health (NIH), clinical trials, peer-reviewed scientific research, laboratory results, and the like. Training data may originate from any number of subjects, wherein the training data may become more robust with increasing datasets. Training data for any machine-learning process described herein may include data recorded by a physiological sensor and/or wearable device and received by computing device as physiological data 108.

Continuing in reference to FIG. 1, intervention machine-learning model 132 may be generated as a function of training the model with the training data to 'learn' how to parse a subject's physiological data 108 (genetics, epigenetics, microbiome, blood panel, nutritional deficiencies, etc.) and detected biomarkers 112 mapped to a malady 116, to model which interventions are predicted to have an effect on malady 116. Intervention machine-learning model 132 may be trained to identify the magnitude of the predicted effect (efficacy). Intervention machine-learning model 132 may be trained with training data to correlate relationships between biomarkers 112 to the predicted efficacy of a predictive intervention.

Continuing in reference to FIG. 1, computing device 104 may determine a plurality of predictive interventions as a function of the intervention category and the physiological data 108 data. A "predictive intervention," as used in this disclosure, is a subject-specific treatment, diet, course-of-action, stand-of-treatment, guidance, advice, regimen, or the like, relating to an intervention category 128, which may address malady 116. Predictive intervention 136 is "subject-specific" in that it is derived from the subject's physiological data 108 data and intended to have efficacy relative to that physiological data 108. Intervention machine-learning model 132 generating predictive intervention 136 may be trained with training data to model intervention category 128 to specific interventions within the category based on predictive efficacy each intervention may have as based on the subject's biomarkers 112. Computing device 104 may determine a plurality of predictive interventions 136 as a function of the intervention category 128 and the physiological data 108 data. Computing device 104 may accept an input of at least a subject's biomarker 112 (and associated physiological data 108), malady 116, and accompanying intervention categories 128 and, using the trained intervention machine-learning process 132, output a plurality of predictive interventions 136. Predictive interventions 136 may become increasingly robust with greater amounts of training data. For instance and without limitation, from more complete sets of biomarkers 112, multiple predictive intervention 136 outputs may be associated, such as a particular medication regimen (dosage, frequency, etc.) may be selected; a specific diet may be selected with a macronutrient (number of calories, grams of macros, etc.) and micronutrient profile (milligram dosage for each vitamin, mineral, etc.); meal timing (timing food consumption, etc.); sleep schedule (when to try to sleep, when to awake, etc.); fitness program recommendation (exercises, repetitions, weight amounts, time spent, etc.), and the like, all of which may be output based on addressing a malady 116. Generating more specific, and greater number of predictive interventions 136 and/or intervention categories 128 may increase the number of combinations and improve the optimization process of identifying efficacious combinations, as described in further detail below.

Continuing in reference to FIG. 1, computing device 104 is configured to generate at least a combination of the plurality of intervention categories. Computing device 104 may use mathematical expressions such as permutations, combinatorics, multiplication, and the like to determine the total number of combinations. Computing device 104 may generate subject-specific combinations using a criteria, such as "not more than one diet included in each combination' or may generically make all potential combinations. For instance with without limitation, if 3 intervention categories were identified: i) class of drugs, ii) diets, and iii) physical activity, and each category has '4' predictive interventions 136, then potential combinations may include 3×4=12 possible listings of one element, or one possible listing of 12 elements, alternatively or additionally, $3^4=64$ possible pairings of three elements exist if order is not prioritized and repetition is allowed, etc. Computing device 104 may generate at least a combination of the plurality of intervention categories, wherein the 'combination' is a single category, but the single category may include any number of predictive interventions 136. Computing device 104 may use a variety of criteria for guiding the combination. Persons skilled in the art may appreciate that with increasing number of intervention categories 128 and predictive interventions 136 the number of combinations may increase exponentially, listing at least thousands of combinations per malady 116, per subject.

Continuing in reference to FIG. 1, generating at least a combination of the plurality of intervention categories may include using a machine-learning process. As described herein, a machine-learning process may include generating an algorithm and/or training a machine-learning model. Computing device 104 may accept an input of a plurality of intervention categories 128 and output a plurality of combinations. Computing device 104 may use a machine-learning process to generate each available combination using a set of rules, or criteria, for instance eliminating certain combinations as they are generated. Machine-learning process may include identifying and/or modeling relationships identified in training data relating to intervention category 128 combination and physiological data 108, such as confining the solutions relative to drug allergies, conflicting medications/diets, fitness recommendations that are impossible for subject, etc. Such training data may include relationships between intervention categories 128 and subject-specific efficacy of combinations thereof. Training data may be retrieved by computing device 104 from an online research database, among other sources, as described above. Training data may be retrieved from a database of alike subjects, wherein subjects may be categorized using a classifier according to similarities in physiological data 108 data, wherein similar solutions may exist between subjects. Training data may be received from a subject, for instance as data from a wearable device, physiological sensor, etc. Training data may include relationships such as the effect of certain foods on medication efficacy, for instance and without limitation, the relationship between citrus fruits (grapefruit, oranges, etc.) may affect the efficacy and metabolism of cholesterol drugs (statins), blood pressure medications (nifedipine), and immunosuppressants (cyclosporine). In such an example, a machine-learning process may use training data to guide the combination of intervention categories 128, for instance, identifying a relationship wherein each time a medication category is selected for a malady 116 relating to high cholesterol and/or hypertension, a diet category may be selected to assist in improving the efficacy of the medication. Furthermore, new intervention categories may be determined by identifying effects such as 'the effect of citrus fruits on medications' using machine-learning, wherein new combinations are identified within training data.

Continuing in reference to FIG. 1, computing device 104 is configured to assign efficacy values to the combination of the plurality of intervention categories as a function of addressing the malady 116. An "efficacy value," as used in this disclosure, is a measure of efficacy associated with an intervention combination. Efficacy value 140 may include magnitude of intended effect, for instance if x milligram (mg) dosage is intended for an individual of a specific bodyweight, sex, age, then efficacy value 140 may include magnitude of efficacy considering subject's physiological data 108. An efficacy value 140 may include any qualitative and/or quantitative measure, metric, and/or parameter, for instance and without limitation, a binary ("yes"/"no") assignment, a numerical value, function of values, vector, array, matrix, or the like. An efficacy value 140 may include an intervention category such as "diet", "antibiotic", and the like, or may include predictive interventions 136 such as "ketogenic diet", "plant-based diet", "lactose-free diet", "beta-lactam inhibitor," "aminoglycoside", etc. Efficacy value 140 may include a percentage or percentile determination, for instance and without limitation, a 90% effectiveness for a particular therapy when combined with a particular amount of REM-cycle sleep per week in addressing a particular mental illness. Efficacy value 140 may include a dimensionless numerical score that is used for direct comparison of magnitude of effect between combinations, for instance where therapy is a score of 50 and diet is a score of 15, and in combination are 60. In such an example, the combination is more efficacious than each individually, and computing device 104 would determine the effect the combination has on efficacy.

Continuing in reference to FIG. 1, assigning efficacy values 140 may include determining the efficacy for each combination of the plurality of intervention categories 128 in addressing malady 116. Computing device 104 may determine the efficacy of each combination of interventions categories and/or predictive interventions. Computing device 104 may determine the efficacy by retrieving, for instance, using a web browser and the Internet, an expected magnitude of effect for an intervention category and/or for each predictive intervention within each category. In such an example, computing device 104 may retrieve a medication dosage and frequency, a dietary recommendation schedule, etc., and determine by how much the malady 116 is addressed with each. In non-limiting illustrative examples, a bacterial infection treated with $3x$ daily medication for 21 consecutive days may result in an output describing each dosage addressing the malady 116 (bacterial infection) by approximately 1.59%, or approximately 4.8% per day, wherein penalties may incur depending on skipping dosages, aberrant frequency, etc. Computing device 104 may then determine how this efficacy changes with physiological data 108, for instance the presence of alike bacteria in microbiome, medical history of bacterial infections with antibiotic resistances, diets with elements that reduce the effect of the antibiotic, side effects from other medications, and the like. Computing device 104 may determine how efficacy changes when combined with other interventions, such as diet, exercise, sleep, lifestyle changes, etc. and recalculate efficacy value 140 depending on the combination generated.

Continuing in reference to FIG. 1, computing device 104 may determine relationships in efficacy using a machine-learning process. For instance and without limitation, when mapping the effect each intervention may have on other interventions in combination, a machine-learning process may be used. Training data for such a machine-learning process may include data describing the effect of a medication, therapy, etc. on a second intervention. For instance and without limitation, the efficacy of adopting a fitness regimen with a low-sugar diet for weight loss or addressing obesity, in combination the efficacy of the other may be boosted. Each intervention may have a combinatorial effect on efficacy, wherein a diet alone may moderately assist with weight loss, and regular exercise may also help, but together an additive, synergistic effect may be observed, and such an effect may be identified and quantified using a machine-learning process. Training data for such a machine-learning process may be retrieved from a database, for instance from PubMed (NIH) research repository using a web browser and the Internet. Training data may originate from a subject questionnaire, wearable device, and/or physiological sensor data, tracking weight loss, BMI, calories, etc., as subjects employ diet changes and exercise. Computing device 104 may perform a machine-learning algorithm, such as a supervised machine-learning algorithm, unsupervised machine-learning algorithm, among other algorithms, as described in further detail below, to parse physiological data 108 data, for instance from a plurality of alike subjects, and determine an effect (response) for each intervention in each intervention category 128, and combinations thereof.

Continuing in reference to FIG. 1, assigning efficacy values 140 may include training an intervention machine-learning model with training data that includes a plurality of data entries wherein each data entry correlates intervention efficacy to numerical value scales. Intervention machine-learning model 144 may include a classifier that is used for classifying intervention categories 128 to numerical value scales. A classifier, as described above, is a machine learning model that combines a discovery component (algorithm that matches an intervention category 128 to a numerical scale) with a learning component (such as performing supervised learning, reinforcement learning, unsupervised learning, etc.), as described in further detail below. An intervention machine-learning model 144 may identify a numerical scale of efficacy for addressing each malady 116. For instance, a malady 116 may include a disease which there is no known cure, wherein the malady 116 remains as a chronic co-morbidity that a subject must adapt. In such an example, the efficacy value 140 may be affected by the understanding that the malady 116 cannot be 'solved'. Thus, the standard for 'efficacy' may be related to magnitude of addressing symptoms, improving subject comfort with the co-morbidity, etc. Whereas an acute, curable malady 116 such as a viral or bacterial infection may have a standard numerical scale where the magnitude is relative to the ability to cure, or 'solve', the malady 116. In such cases, the numerical value scale for 'grading' efficacy value 140 or each, or combinations thereof, may be relative to the malady 116 being addressed; intervention machine-learning model 144 may be used to classify each to an appropriate numerical scale.

Continuing in reference to FIG. 1, the intervention machine-learning model 144 may include a machine-learning model trained with training data that includes a plurality of data entries wherein each data entry models predictive interventions 136 to numerical scales. Training data may include intervention categories 128 and predictive interventions 136 for a malady 116, including effects. For instance, training data for soft-tissues injuries may include methodologies such as 'RICE method' (rest, ice, compression, elevation), dietary recommendations such as '500 mg daily increased potassium supplementation', fitness recommendations such as 'light stretching', medication recommendations such as 'acetaminophen', and the like, where each is associated with a degree of efficacy. Each may be associated with a degree of efficacy, for instance by searching and retrieving data corresponding to 'recommendation dosages' from drug information, sports injury methodologies, etc. Efficacy may be retrieved using computing device 104 with a web browser and the Internet, efficacy may be retrieved from a database including a table of values relating dose-to-effect.

Continuing in reference to FIG. 1, efficacy may be derived using a machine-learning process, wherein a numerical scale for the range of efficacies is derived, or 'learned', from training data. For instance, 'acetaminophen' may be rated for efficacy on a scale using dosages, such as 500 mg vs 1000 mg vs 2000 mg, and graphed as a function of body weight, age, sex, among other data, in the subject's physiological data 108 used to derive an efficacy value 140 from the relationship. Such a relationship may be represented as a series of functions of values, a normal distribution of alike subjects, as percentiles, and the like. Each category/intervention may have an efficacy associated as a function of time, for instance directly after a soft-tissue injury the 'RICE method' may receive a high efficacy value 140, and 'light stretching' may receive a very low efficacy value 140. In such an example, timing is important to the efficacy value 140. Combining the 'RICE method' performed twice daily within the first 7 days of injury and 'light stretching' no sooner than 7 days, and 500 mg potassium supplementation to reduce bruising and improve vascular trauma, in combination, may result in an efficacy value 140 greater than each individually. In instances where efficacy is not easily retrievable by computing device 104, a machine-learning model may be trained to determine patterns of efficacy and a value assigned based on the patterns. For instance, the 'RICE method' may always be performed first, and subjects may recover prior to the 'light stretching' phase, and thus that category may be discovered to be less efficacious and receive little benefit to add in combination to 'RICE method'. A machine-learning model trained with training data (intervention vs recovery) may be used to assign and refine efficacy values 140 for each combination.

Continuing in reference to FIG. 1, numerical scales used to assign efficacy value 140 may include thresholds, above or below which a certain numerical value is assigned. For instance, varying degrees of efficacy between categories may be used to assign efficacy value 140, where a value of 90-100 may completely address a malady 116, from 50-89 may greatly improve but not completely address, below 20 does little, etc. Numerical scales may include "banding" where there are numerical value ranges assigned as a function of a category efficacy. For instance 'diet', 'exercise', and 'weight management' categories may work to prevent future high cholesterol issues and/or assist in controlling cholesterol levels, but only a 'medication' (such as a statin) will truly "solve" the issue. The institution of a combination of intervention categories may result in higher efficacies that, in combination, less frequent and/or lower dosage may be necessary to help balance cholesterol in the future. In such an example, the efficacy value 140 may increase when combining predictive interventions 136 from a 'diet' category, 'drug' category, 'fitness' category, 'weight management' category, etc. This way, a numerical scale of efficacy value 140 for a 'diet' may belong to a lower 'value band', where even the most efficacious diet will not contribute as much as a 'drug' category predictive intervention 136 (such as a statin medication). Additionally, numerical scale "banding" may include partitioning of numerical values, wherein diets are provided values from '0 to 10' and medical treatments are provided '20 to 50' values as their efficacy is rated to be much higher than a diet in addressing certain maladies, for instance diabetes, high cholesterol, cancer, depression, etc.

Continuing in reference to FIG. 1, similarly, in non-limiting illustrative examples, numerical value scale may be determined as a function of physiological data 108. For instance, depending on race, ethnicity, sex, age, fitness level, sleep profile, medication allergies, among other physiological and biological factors, certain medications, diets, and the like, may provide different levels of efficacy on a per-subject basis. In such an instance, intervention machine-learning model 144 may 'learn' to assign category efficacy values 140 and numerical ranges as a function of per-subject efficacy. For instance, a subject with obesity may receive a different efficacy value 140 for adopting a particular diet and/or fitness regimen than an already active subject.

Continuing in reference to FIG. 1, determining efficacy may include retrieving at least a predictive intervention 136 from each intervention category of the combination and assigning an efficacy value 140 as a function of the intervention machine-learning model 144. Intervention machine-learning model 144 may determine a numerical value scale for each category of a combination and assign a value for each individual predictive intervention 136 based on such a scale. For instance, for someone who is diabetic, 'diets' may be scored from 10-20, 'medication' may be scored 20-50, and 'exercise' may be scored 5-15, selecting an intervention from each for a combination may be 'low glycemic index diet' (efficacy value 18), 'anti-diabetic drug' (efficacy value 33), and '2 hour cardio per week' (efficacy value 7). That combination may receive a higher score, for instance in younger adults, or lower score, for instance in geriatric subjects where combining exercise may decrease the efficacy value 140 due to increased risk of injury. In such a case, the combination of interventions may receive a score using a mathematical expression, for instance using addition and a multiplicative scalar to adjust based on physiological data 108. For each category, intervention machine-learning model 144 may learn how to assign '18' to a 'low glycemic index diet', '16' for a 'ketogenic diet', '13' for a 'Paleo diet', etc., based on the efficacies of the full spectrum of diets in the category and how each relates to "diabetes". In such an example, the combination may include an efficacy value 140 of '58', wherein a maximal efficacy combination of the three categories may never exceed '85' as diabetes may not be fully 'cured' with these elements.

Continuing in reference to FIG. 1, assigning values for combinations may include generating an objective function of a plurality of predictive intervention 136 combinations as a function of efficacy in addressing the malady 116, wherein maximizing the objective function maximizes the efficacy value 140 of the combination. An "objective function," as used in this disclosure, is a mathematical function that may be used by computing device 104 to score each possible combination of predictive interventions 136, wherein the objective function may refer to any mathematical optimization (mathematical programming) to select the 'best' element from a set of available alternatives. Selecting the 'best' element from a set of available alternatives may include a combination of predictive interventions 136 which maximizes the efficacy value 140 in addressing a malady 116 in a subject.

Continuing in reference to FIG. 1, an objective function may include performing a greedy algorithm process. A "greedy algorithm" is defined as an algorithm that selects locally optimal choices, which may or may not generate a globally optimal solution. For instance, computing device 104 may select combinations of intervention categories 128 so that values associated therewith are the best value for each category. For instance, in non-limiting illustrative example, optimization may determine the combination of the most efficacious 'medication', 'diet', 'fitness', and 'sleep' categories to provide a combination that may include several locally optimal solutions but may or may not be globally optimal in combination.

Still referring to FIG. 1, objective function may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a subject (lactose intolerance, drug metabolism, etc.), and a linear program may use a linear objective function to calculate combinations, considering how these limitation effect combinations using 'ketogenic diet', etc. In various embodiments, system 100 may determine a set of instructions towards addressing a subject's malady 116 that maximizes a total efficacy score 140 subject to a constraint that there are other competing objectives. For instance, if one 'diet', 'fitness', and/or 'sleep' predictive intervention 136 is selected from each intervention category 128, selecting a second may compete in efficacy (i.e. adopting two or more diets simultaneous may not be feasible). A mathematical solver may be implemented to solve for the set of instructions that maximizes scores; mathematical solver may be implemented on computing device 104 and/or another device in system 100, and/or may be implemented on third-party solver.

With continued reference to FIG. 1, objective function may include minimizing a loss function, where a "loss function" is an expression an output of which a process minimizes to generate an optimal result. For instance, a malady 116 may be set to a nominal value, such as '100', wherein the objective function selects elements in combination that reduce the value to '0', wherein the malady 116 is '100% addressed'. In such an example, 'maximizing' would be selecting the combination of elements that results in the highest efficacy, by minimizing the difference between the efficacy of the combination of elements and the efficacy required to fully address malady 116. As a non-limiting example, computing device 104 may assign variables relating to a set of parameters, which may correspond to efficacy value 140 components as described above, calculate an output of mathematical expression using the efficacy value 140 variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 1, computing device 104 is configured to provide, to the subject, the combination as a function of the efficacy values 140. Computing device 104 may provide the combination using a graphical user interface. A "graphical user interface," as used in this disclosure, is any form of a user interface that allows a subject to interface with an electronic device through graphical icons, audio indicators, text-based interface, typed command labels, text navigation, and the like, wherein the interface is configured to provide information to the subject and accept input from the subject. Graphical user interface may accept subject input, wherein subject input may include an interaction (such as a questionnaire) with a user device. A user device may include computing device 104, a "smartphone," cellular mobile phone, desktop computer, laptop, tablet computer, internet-of-things (JOT) device, wearable device, among other devices. User device may include any device that is capable for communicating with computing device 104, database, or able to receive, transmit, and/or display predictive intervention 136, for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, etc.), and the like.

Continuing in reference to FIG. 1, providing the predictive intervention 136 may include generating an ordering of the plurality of combinations based on efficacy value 140. An "ordering," as used in this disclosure, is a ranked list that provides an order to the elements of the list. An ordering may include an ordering of a plurality of predictive interventions 136. An ordering may include a list of elements ordered by efficacy value 140. Computing device 104 may generate an ordering, for instance and without limitation, by generating a file that lists a plurality of predictive interventions 136, and combinations thereof, by descending efficacy value 140 for malady 116. Computing device 104 may use a machine-learning process, algorithm, program, and/or model, for instance as performed by a machine-learning module, as described in further detail below. Such a machine-learning process (such as a supervised machine-learning process) may 'learn' to order a plurality of predictive intervention 136 (and combinations thereof), as a function of a variety of criteria. Ordering criteria may include feasibility of combining, difficulty of adaptation, cost factors, adherence to lifestyle, etc. Ordering criteria may include subject input, for instance selecting particular diets, exercise recommendations, sleep schedules, among other predictive interventions 136. Ordering elements may include generating a queue, wherein a queue is a collection of elements that are maintained in a particular sequence and can be modified by the addition and removal of elements. For instance and without limitation, completing a first element in the queue, removes it from the queue and replaces with the second most efficacious element. Ordering may be performed in a variety of methods to logically organize predictive intervention 136 for subject to follow a combination of elements to maximize addressing malady 116.

Figure 2:
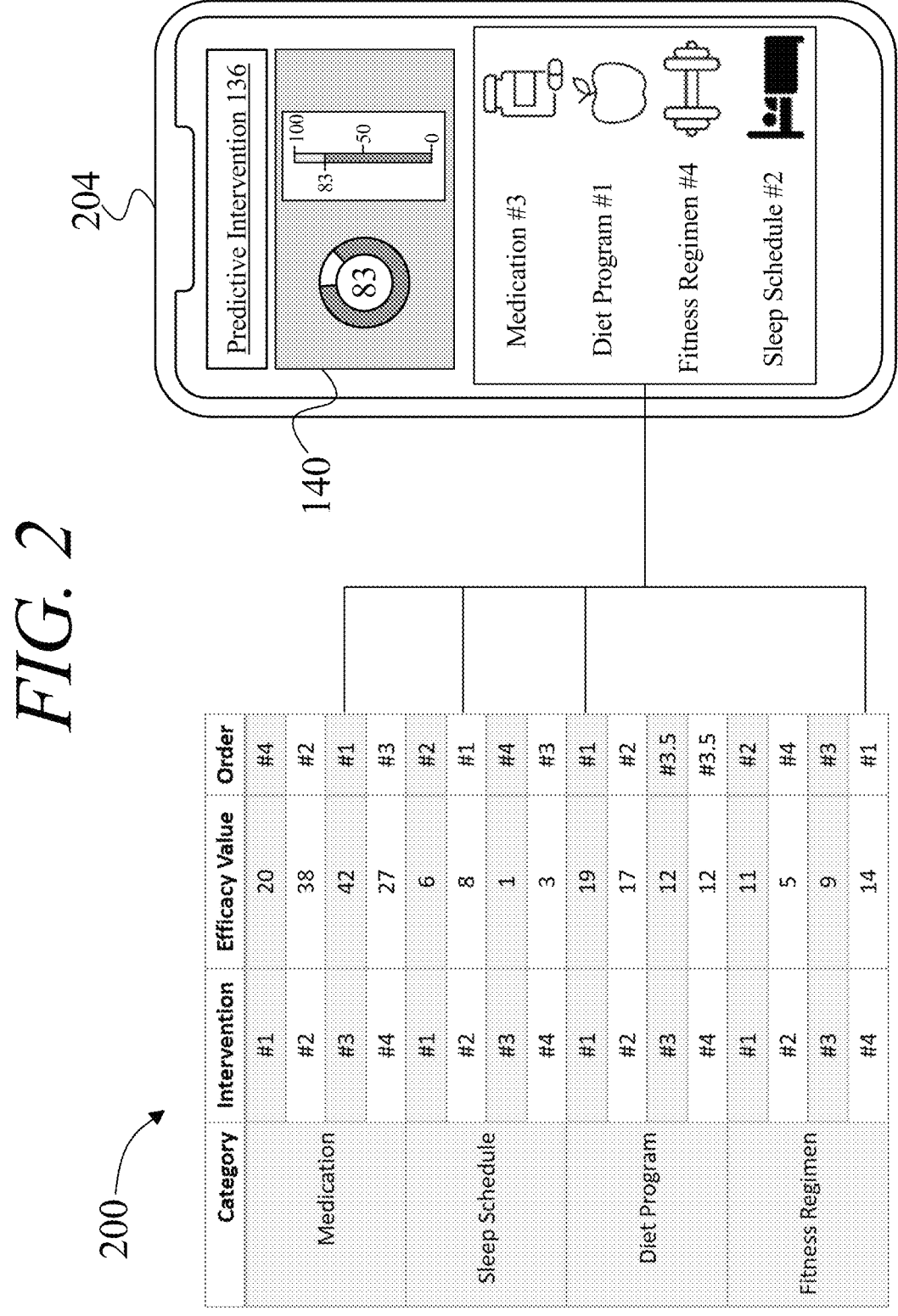
FIG. 2 is a diagrammatic illustration of a non-limiting exemplary embodiment of a user device providing predictive intervention.

Referring now to FIG. 2, a non-limiting exemplary embodiment 200 of a user device providing predictive intervention 136 is illustrated. Providing the predictive intervention 136 may include generating a representation, via a graphical user interface, of the predictive intervention 136, which may include any suitable graphical user interface, as described herein. Generating the representation may include graphical icons, numerical values, hyperlinked elements, for instance wherein selecting may link to a document, website, or the like. In non-limiting exemplary embodiments, system 100 may determine efficacy values for each element of a plurality of intervention categories 128 and organize based on an efficacy value 140 derived from a numerical scale for each category, and generate combinations of the plurality, and select the most efficacious combinations, and provide the combination as the predictive intervention 136. For instance, as depicted in FIG. 2, of the 4 categories (n), and 4 elements (m) in each, computing device 104 may generate a variety of combinations using combinatorics and/or permutations, such as $n^m$, $P(n, m)=n!/(n-m)!$; for $n \geq m \geq 0$, and other formulas. For instance, if '4' intervention categories 128 exist, and '4' predictive interventions 136 exist in each, and order and repetition are not accounted for, there may exist up to 256 different combinations, each of which may have an associated efficacy value 140. Predictive intervention 136 may include any intervention strategy as a function of a calculated ordering, which may combine different strategies according to the determined relationships. The predictive interventions 136 may be provided in a logical ordering, instruction set, and the like, via the user device 204.

Figure 3:
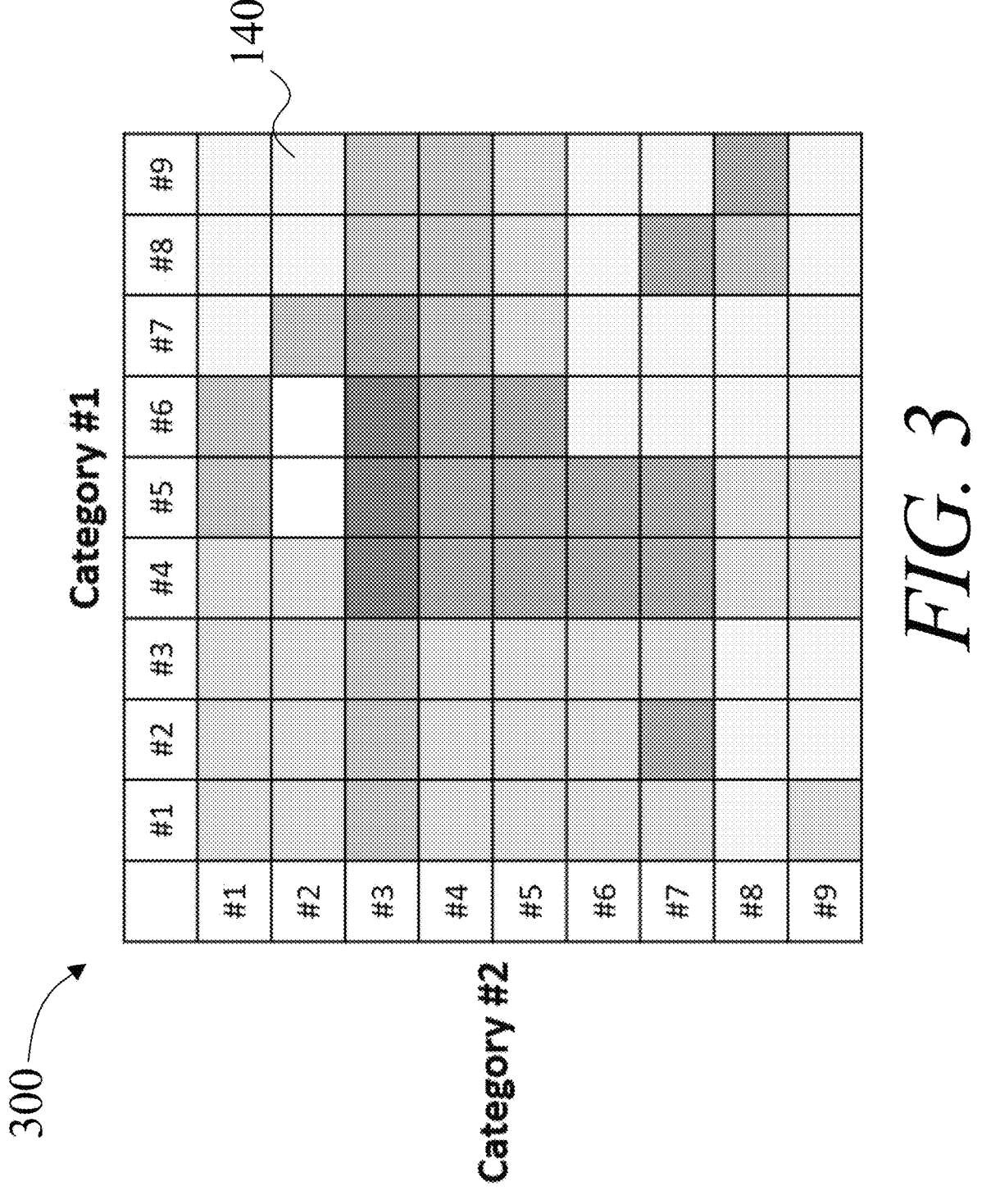
FIG. 3 is a diagrammatic illustration of a non-limiting exemplary embodiment of predictive intervention combinations.

Referring now to FIG. 3, a non-limiting exemplary embodiment 300 of a plurality of predictive intervention 136 combinations is illustrated. Each combination may have an associated efficacy value 140 that is calculated from a combined efficacy determined for each combination. Computing device 104 may generate, for instance and without limitation, a 'heat map' for determining efficacy of a combination of a plurality of combinations. For instance, as shown in FIG. 3, #4, #5, and #6 of category #1 combined with #3 of category #2 represent the top four combinations, ranked by efficacy, within the combination of 81 elements (one of each category combined). Additionally, a combination of these 81 elements (or the four best), may be combined with a third element, and a fourth . . . wherein the number of combinations increases exponentially and increasingly complicated relationships between efficacy emerge. Efficacy values for a plurality of combined elements (predictive intervention 136) may be accomplished with an objective function, as descried above. Alternatively or additionally, computing device 104 may use a machine-learning process, as described in further detail below, to iteratively calculate the most efficacious combination.

Figure 4:
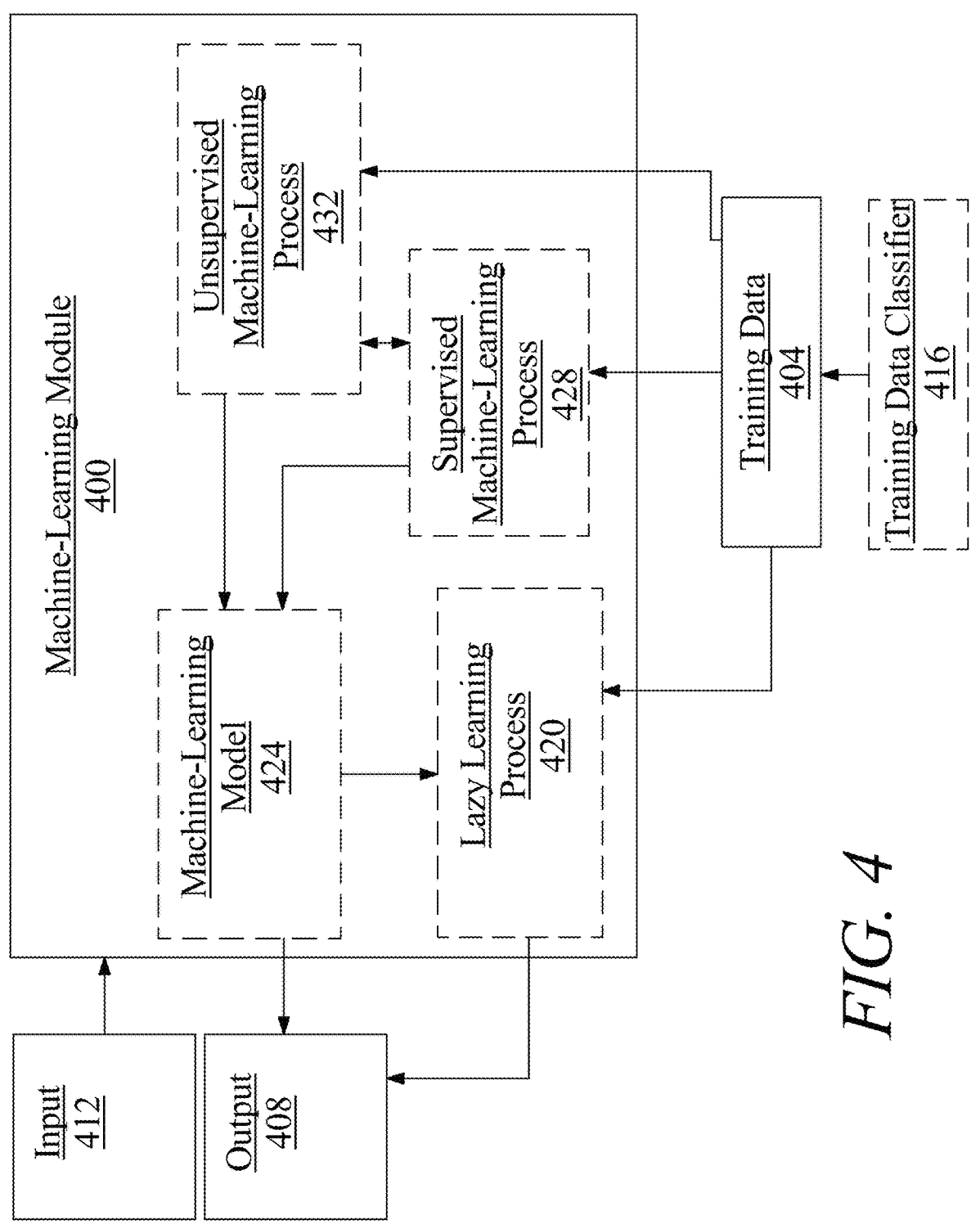
FIG. 4 is a block diagram of a non-limiting exemplary embodiment of a machine-learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm that will be performed by a computing device/module to produce outputs 408 given data provided as inputs 412; this is in contrast to a non-machine learning software program where the commands to be executed are determined in advance by a subject and written in a programming language.

Still referring to FIG. 4, "training data," as used herein, is data containing correlations that a machine-learning process may use to model relationships between two or more categories of data elements. For instance, and without limitation, training data 404 may include a plurality of data entries, each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail herein. Training data 404 used by machine-learning module 400 may correlate any input data as described in this disclosure to any output data as described in this disclosure.

Further referring to FIG. 4, training data may be filtered, sorted, and/or selected using one or more supervised and/or unsupervised machine-learning processes and/or models as described in further detail herein; such models may include without limitation a training data classifier 416. Training data classifier 416 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a process whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to elements that characterizes a sub-population, such as a subset of physiological data 108 (such as gene expression patterns as it relates to biomarkers 112) as a function of maladies 116, intervention categories, predictive interventions 136, numerical value scales, sets of alike subjects, and/or other analyzed items and/or phenomena for which a subset of training data may be selected.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements, such as classifying physiological data 108 elements to a biomarkers 112 and assigning a value as a function of some ranking association between elements (physiological data 108 to biomarker 112, biomarker 112 to malady 116, etc.). Lazy learning may implement any suitable lazy learning algorithm, including without limitation a K-nearest neighbors algorithm, a lazy naive Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used as to derive numerical scales for providing numerical values to efficacy values 140, as described above, to "learn" the upper and lower limits to the scale, the increments to providing scoring, and the criteria for increasing and decreasing the efficacy value 140. A machine-learning model may be used to "learn" which elements of physiological data 108 belong to which biomarker 112 class, which biomarkers 112 relate to which malady 116, and which intervention categories relate to each malady 116.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a plurality of biomarkers 112 (potentially classified into categories), as described above as inputs, maladies 116 outputs as it related to classified parameters, and a ranking function representing a desired form of relationship to be detected between inputs and outputs (figure of merit 124); ranking function may, for instance, seek to maximize the probability that a given input and/or combination of elements inputs is associated with a given output to minimize the probability that a given input is not associated with a given output, for instance in finding the most suitable malady 116. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes may include at least an unsupervised machine-learning process 432. An unsupervised machine-learning process 432, as used herein, is a process that derives inferences in datasets without regard to labels; as a result, an unsupervised machine-learning process 432 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 4, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 404.

Figure 5:
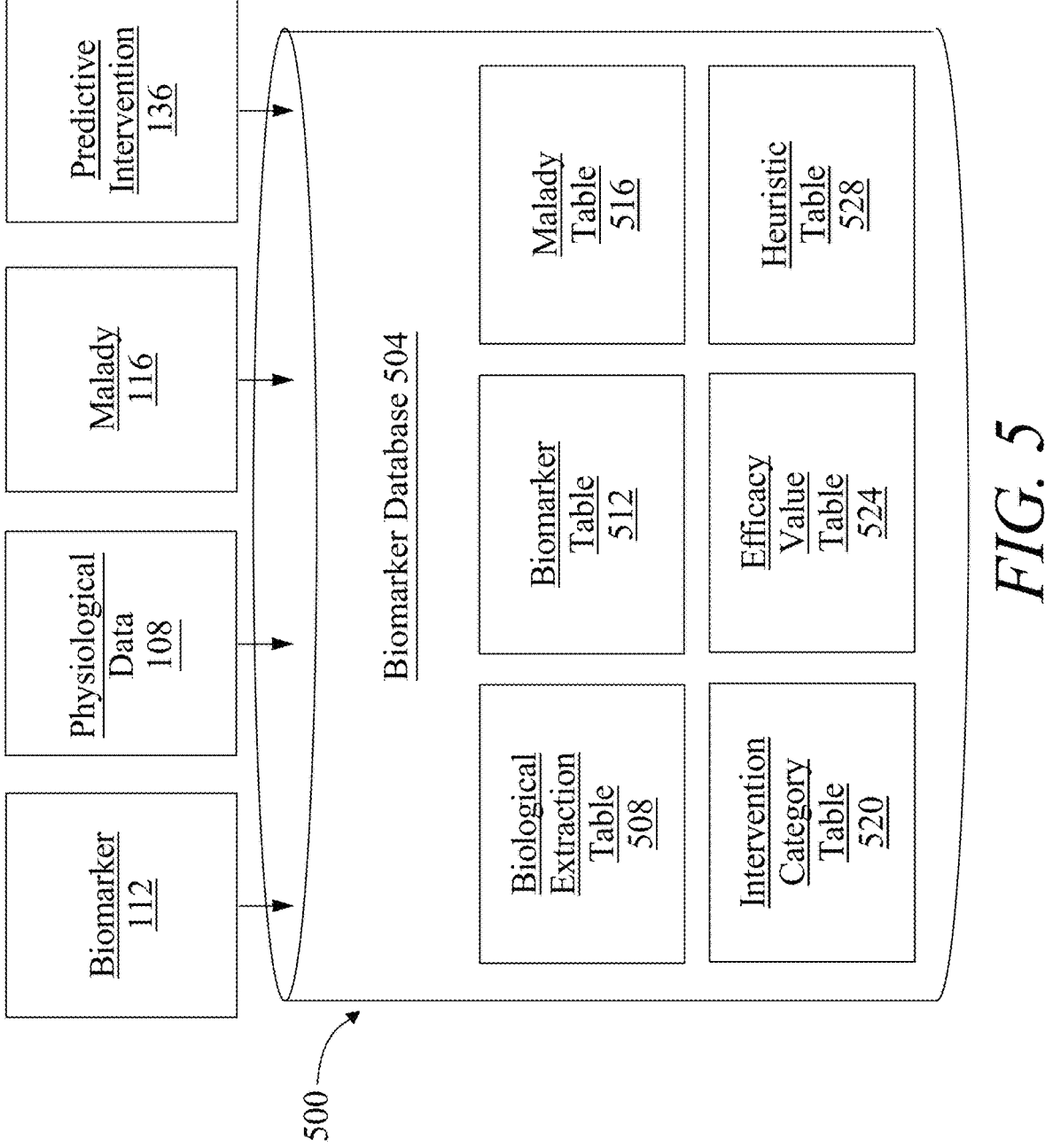
FIG. 5 is a block diagram of a non-limiting exemplary embodiment of a biomarker database.

Referring now to FIG. 5, a non-limiting exemplary embodiment 500 of a biomarker database 504 is illustrated. Physiological data 108 for a plurality of subjects, for instance for generating a biomarker classifier 120, may be stored and/or retrieved in biomarker database 504. Physiological data 108 data from a plurality of subjects for generating training data 404 may also be stored and/or retrieved from a biomarker database 504. Computing device 104 may receive, store, and/or retrieve training data 404, wearable device data, and the like, Computing device 104 may store and/or retrieve biomarker classifier 120, physiological data 108, efficacy values 140, classifiers, among other determinations, I/O data, models, and the like, in biomarker database 504. Biomarker database 504 may be implemented, without limitation, as a relational database, a key-value retrieval database such as a NOSQL database, or any other format or structure for use as a database that a person skilled in the art would recognize as suitable upon review of the entirety of this disclosure. Biomarker database 504 may alternatively or additionally be implemented using a distributed data storage protocol and/or data structure, such as a distributed hash table and the like. Biomarker database 504 may include a plurality of data entries and/or records, as described above. Data entries in a biomarker database 504 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure. Computing device 104 may retrieve any determinations, as described herein, from the biomarker database 504, such as biomarkers 112, maladies 116, figure of merit 124, intervention category 128, predictive interventions 136, efficacy values 140, and the like.

Further referring to FIG. 5, biomarker database 504 may include, without limitation, physiological data table 508, biomarker table 512, malady table 516, intervention category table 520, efficacy value table 524, and/or heuristic table 528. Determinations by a machine-learning process, machine-learning model, ranking function, and/or classifier, may also be stored and/or retrieved from the biomarker database 504, for instance in non-limiting examples, biomarker 112, malady 116, and figure of merit 124, according to a particular physiological data 108 classification, and the like. As a non-limiting example, biomarker database 504 may organize data according to one or more instruction tables. One or more biomarker database 504 tables may be linked to one another by, for instance in a non-limiting example, common column values. For instance, a common column between two tables of biomarker database 504 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 5, in a non-limiting embodiment, one or more tables of an biomarker database 504 may include, as a non-limiting example, a physiological data table 508, which may include categorized identifying data, as described above, including genetic data, epigenetic data, microbiome data, physiological data, and the like. Physiological data table 508 may include physiological data 108 categories according to biomarker 112 categories, may include linked tables to mathematical expressions that describe the impact of each physiological data 108 datum on a biomarker 112, for instance threshold values for gene expression, etc. One or more tables may include biomarker table 512, which may include data regarding physiological data 108, thresholds, values, malady 116 categorizations, and the like, that system 100 may use to calculate, derive, filter, retrieve and/or store physiological data 108 data for determining disease, symptoms, therapeutics, etc. One or more tables may include malady table 516, which may include data regarding thresholds, cutoffs, etc., for determining the presence of a malady 116 according to physiological data 108 data. Malady table 516 may include data from alike subjects with similar physiological data 108, and the like, that system 100 may use to calculate, derive, filter, retrieve and/or store intervention categories and determine figure of merit 124 of a malady for biomarkers 112. One or more tables may include intervention category table 520, which may include data intervention categories 128 and numerical value scales for measuring efficacy, and the like, that system 100 may use to calculate, derive, filter, retrieve and/or store predictive interventions 136, and combinations thereof. One of more tables may include an efficacy value table 524, which may include numerical values, and/or outputs, determinations, variables, and the like, organized into subsets of data for generating efficacy values 140 for individual predictive interventions 136, intervention categories 128, numerical scales, and the like. One or more tables may include, without limitation, a heuristic table 528, which may organize rankings, scores, models, outcomes, functions, numerical values, scales, arrays, matrices, and the like, that represent determinations, probabilities, metrics, parameters, values, and the like, include one or more inputs describing potential mathematical relationships, as described herein.

Figure 6:
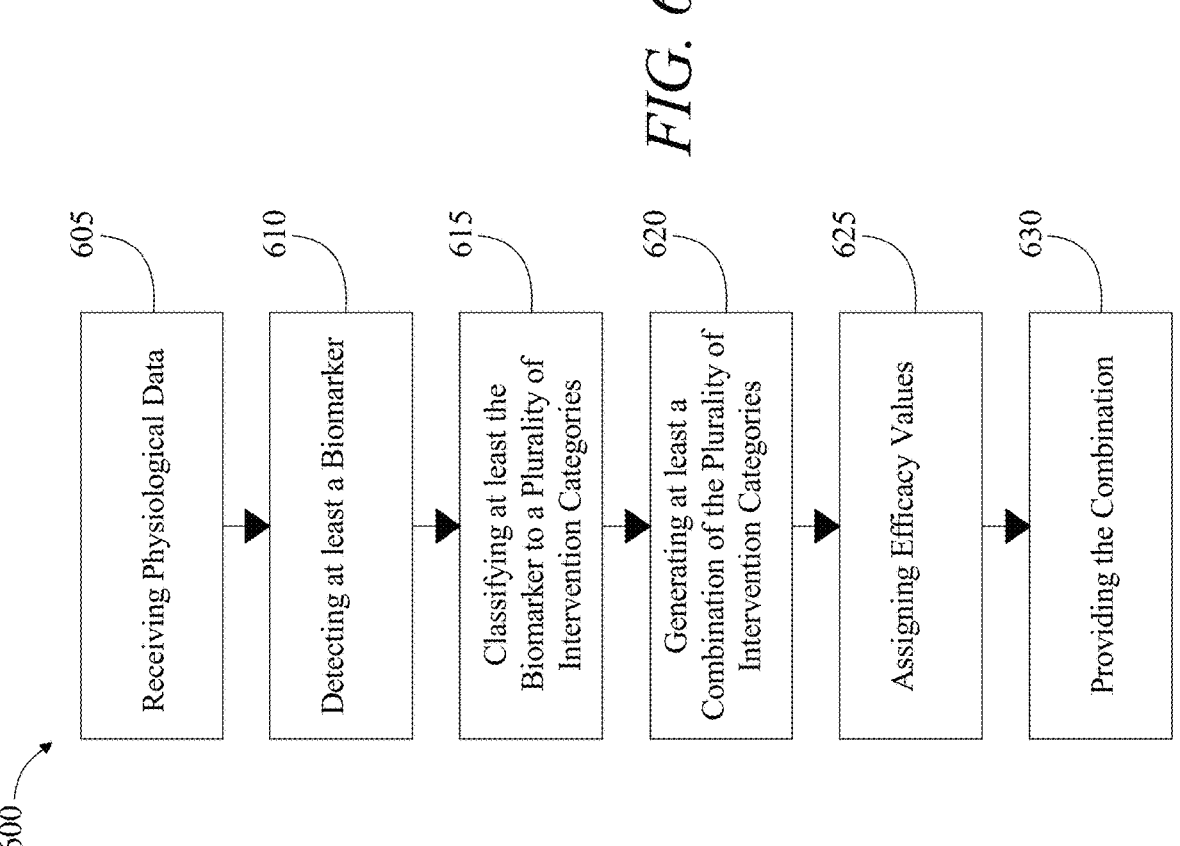
FIG. 6 is a flow diagram illustrating an exemplary work flow of a method of determining a predictive intervention using biomarkers.

Referring now to FIG. 6, a non-limiting exemplary embodiment 600 of a method for determining a predictive intervention using biomarkers is illustrated. At step 605, computing device 104 is configured for receiving physiological data 108 data from a subject; this may be implemented, without limitation, as described above in FIGS. 1-5.

Still referring to FIG. 6, at step 610, computing device 104 is configured for detecting, using the physiological data 108 data, at least a biomarker 112 linked to a malady 116. Detecting at least the biomarker 112 may include generating a biomarker classifier 120 using a classification machine-learning process to categorize physiological data 108 data to malady biomarkers 112. Detecting the malady 116 may include indicating a figure of merit 124 for a plurality of maladies 116 as they correlate to at least the subject biomarker 112 and selecting the malady 116 as a function of figure of merit 124; this may be implemented, without limitation, as described above in FIGS. 1-5.

Continuing in reference to FIG. 6, at step 615, computing device 104 is configured for classifying at least the biomarker 112 to a plurality of intervention categories 128 for the malady 116, wherein each intervention category 128 of the plurality of intervention categories 128 is a distinct classification of intervention based on physiological data 108 data. Classifying the biomarker 112 to at least the intervention category 128 may include training an intervention machine-learning model 132 with training data that includes a plurality of data entries wherein each data entry correlates biomarkers 112 to predictive interventions 136, and determining a plurality of predictive interventions 136 as a function of the intervention category 128 and the physiological data; this may be implemented, without limitation, as described above in FIGS. 1-5.

Continuing in reference to FIG. 6, at step 620, computing device 104 is configured for generating at least a combination of the plurality of intervention categories 128; this may be implemented, without limitation, as described above in FIGS. 1-5.

Continuing in reference to FIG. 6, at step 625, computing device 104 is configured for assigning efficacy values 140 to the combination of the plurality of intervention categories 128 as a function of addressing the malady 116. Assigning efficacy values 140 may include determining the efficacy for each combination of the plurality of intervention categories 128 in addressing malady 116. Assigning efficacy values 140 may include training an intervention machine-learning model 144 with training data that includes a plurality of data entries wherein each data entry correlates intervention efficacy to numerical value scales. Determining efficacy may include retrieving at least a predictive intervention from each intervention category of the combination and assigning an efficacy value as a function of the intervention machine-learning model 144. Assigning values for combinations may include generating an objective function of a plurality of predictive intervention combinations as a function of efficacy in addressing the malady, wherein maximizing the objective function maximizes the efficacy value of the combination; this may be implemented, without limitation, as described above in FIGS. 1-5.

Continuing in reference to FIG. 6, at step 630, computing device 104 is configured for providing, to the subject, the combination as a function of the efficacy values 140. Providing the predictive intervention 136 may include generating an ordering of the plurality of combinations based on efficacy value 140. Providing the predictive intervention 136 may include generating a representation, via a graphical user interface, of the predictive intervention 136; this may be implemented, without limitation, as described above in FIGS. 1-5.

It is to be noted that any one or more of the aspects and embodiments described herein may be conveniently implemented using one or more machines (e.g., one or more computing devices that are utilized as a subject computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
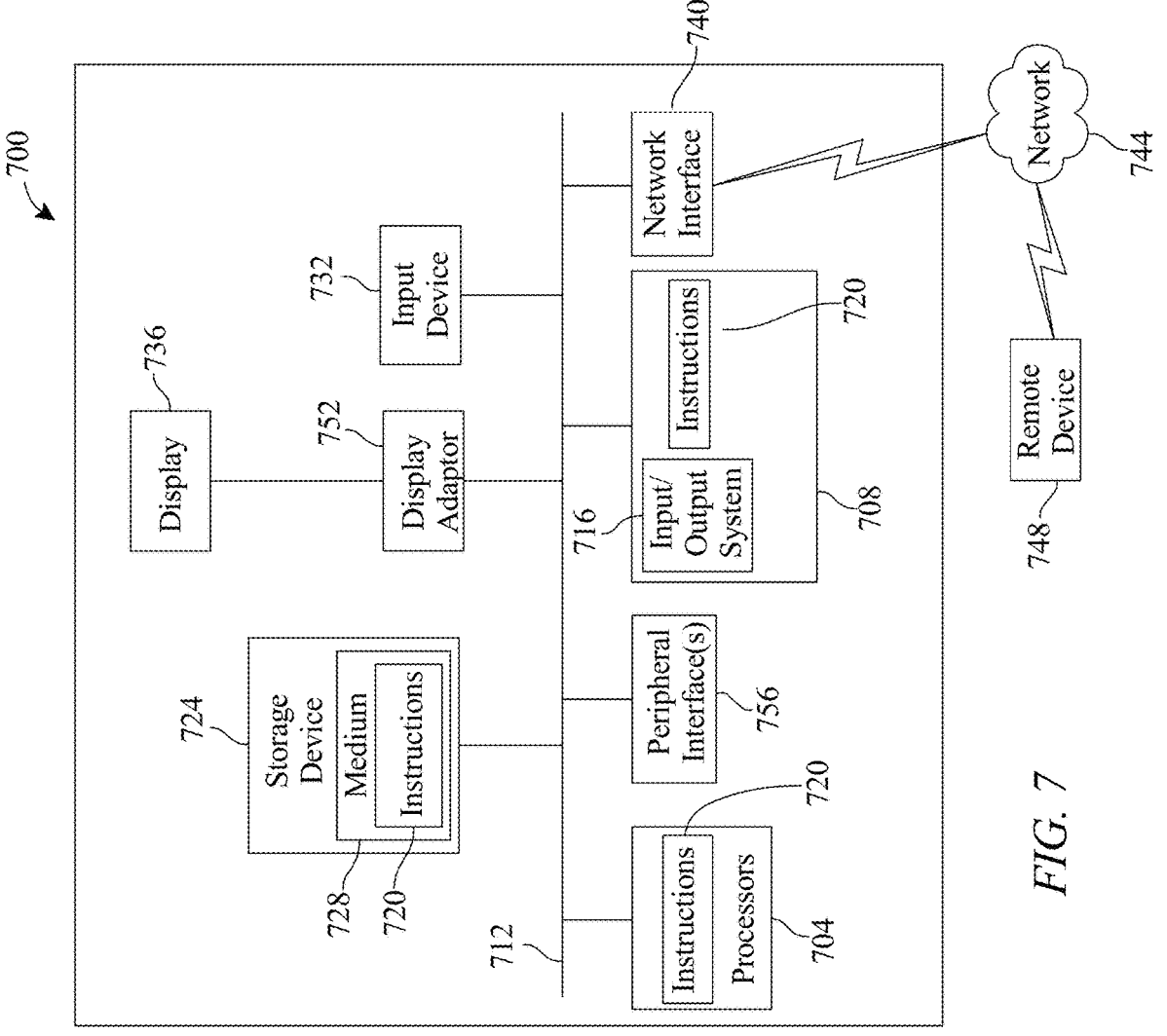
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a subject of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a subject selection device for selecting one or more graphical representations in a graphical interface as described above.

A subject may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756.

Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for determining a predictive intervention using biomarkers, the system comprising a computing device, wherein the computing device is configured to:

receive physiological data from a subject, wherein the physiological data is received from at least a physiological sensor wherein the physiological data comprises multi-dimensional biomarker data comprising one or more of a genetic, metabolic, immunological, and blood panel data;

identify a malady, as a function of the physiological data, wherein identifying the malady further comprises:

indicating a figure of merit for a plurality of maladies as they correlate to at least a biomarker, wherein the figure of merit is a quantity used to characterize a fit of a malady for at least a biomarker detected in the physiological data, wherein the figure of merit includes a percentile that indicates a likelihood the malady fits a particular pattern of biomarkers, wherein the computing device determines a match between the malady and physiological data as a function of the percentile, wherein the figure of merit includes a quantifier derived from a machine learning model that informs the system on selecting the malady from the physiological data;

selecting the malady as a function of the figure of merit;

classify the malady to a plurality of intervention categories for the malady, wherein each intervention category of the plurality of intervention categories is a distinct classification based on physiological data utilizing an intervention machine-learning model which comprises:

receiving intervention training data, wherein the intervention training data correlates a plurality of biomarker data to a plurality of intervention category data;

iteratively training the intervention machine-learning model with the intervention training data and includes retraining the intervention machine-learning model with feedback from previous iterations of the intervention machine-learning model, wherein the intervention machine-learning model is trained further to derive a numerical scale for providing numerical values to determine an efficacy value of an intervention category and to learn:

upper and lower limits to the scale;

increments to determining the efficacy value; and a criteria for increasing and decreasing the efficacy value, wherein training the intervention machine-learning model with the training data comprises:

applying the training data to input nodes of the intervention machine learning model;

creating connections between a plurality of nodes of the intervention machine-learning model; and adjusting the connections and weights between the plurality of nodes of the intervention machine-learning model to produce desired values at output nodes of the intervention machine learning model;

identifying, using the intervention machine-learning model a plurality of intervention categories correlated to the identified malady;

generate at least a combination of the plurality of intervention categories using a machine learning model comprising:

receiving training data, wherein the training data correlates a plurality of relationship data to a plurality of intervention category data for the malady generated from the trained intervention machine-learning model;

iteratively training the machine learning model with the training data which includes retraining the machine learning model with feedback from previous iterations of the machine learning model;

assign efficacy values, using the intervention machine-learning model, to the at least a combination of the plurality of intervention categories as a function of addressing the malady; and display, to the subject, a predictive intervention by generating a representation, via a graphical user interface, which includes a combination as a function of the assigned values, wherein the combination comprises, ordering, the plurality of interventions based of a variety of criteria including at least a difficulty of adaption criterion.

2. The system of claim 1, wherein classifying the malady to at least the intervention category further comprises identifying a plurality of predictive interventions as a function of the physiological data and the intervention category.

3. The system of claim 1, wherein assigning efficacy values further comprises determining the efficacy for each combination of the plurality of intervention categories in addressing malady.

4. The system of claim 1, wherein assigning efficacy values further comprises:

training an intervention machine-learning model with training data that includes a plurality of data entries wherein each data entry correlates intervention efficacy to numerical value scales; and assigning efficacy values to the plurality of predictive interventions as a function of the intervention machine-learning model.

5. The system of claim 4, wherein determining efficacy further comprises retrieving the plurality of predictive interventions from each intervention category of the combination and assigning an efficacy value as a function of the intervention classifier.

6. The system of claim 1, wherein assigning values for at least the combination further comprises:

determining a plurality of predictive intervention combinations; and generating an objective function of the plurality of predictive intervention combinations as a function of efficacy in addressing the malady, wherein maximizing the objective function maximizes the efficacy value of the combination.

7. The system of claim 1, wherein providing the predictive intervention further comprises generating an ordering of the plurality of combinations based on efficacy value.

8. A method for determining a predictive intervention using biomarkers, the method comprising:

receiving, by a computing device, physiological data from a subject, wherein the physiological data is received from at least a physiological sensor wherein the physiological data comprises multi-dimensional biomarker data comprising one or more of a genetic, metabolic, immunological, and blood panel data;

identifying, by the computing device, a malady, as a function of the physiological data, wherein identifying the malady further comprises:

indicating a figure of merit for a plurality of maladies as they correlate to at least a biomarker, wherein the figure of merit is a quantity used to characterize a fit of a malady for at least a biomarker detected in the physiological data, wherein the figure of merit includes a percentile that indicates a likelihood the malady fits a particular pattern of biomarkers, wherein the computing device determines a match between the malady and physiological data as a function of the percentile, wherein the figure of merit includes a quantifier derived from a machine learning model that informs a system on selecting the malady from the physiological data;

selecting the malady as a function of the figure of merit;

classifying, by the computing device, the malady to a plurality of intervention categories for the malady, wherein each intervention category of the plurality of intervention categories is a distinct classification based on physiological data utilizing an intervention machine-learning model which comprises:

receiving intervention training data, wherein the intervention training data correlates a plurality of biomarker data to a plurality of intervention category data;

iteratively training the intervention machine-learning model with the intervention training data and includes retraining the intervention machine-learning model with feedback from previous iterations of the intervention machine-learning model, wherein the intervention machine-learning model is trained further to derive a numerical scale for providing numerical values to determine an efficacy value of an intervention category and to learn: upper and lower limits to the scale;

increments to determining the efficacy value; and a criteria for increasing and decreasing the efficacy value, wherein training the intervention machine-learning model with the training data comprises:

applying the training data to input nodes of the intervention machine learning model;

creating connections between a plurality of nodes of the intervention machine-learning model; and adjusting the connections and weights between the plurality of nodes of the intervention machine-learning model to produce desired values at output nodes of the intervention machine learning model;

identifying, using the intervention machine-learning model a plurality of intervention categories correlated to the identified malady;

generating, by the computing device, at least a combination of the plurality of intervention categories using a machine learning model comprising:

receiving training data, wherein the training data correlates a plurality of relationship data to a plurality of intervention category data for the malady generated from the trained intervention machine-learning model;

iteratively training the machine learning model with the training data which includes retraining the machine learning model with feedback from previous iterations of the machine learning model;

assigning, using the intervention machine-learning model, by the computing device, efficacy values to the at least a combination of the plurality of intervention categories as a function of addressing the malady; and displaying, by the computing device, to the subject, a predictive intervention by generating a representation, via a graphical user interface, which includes a combination as a function of the assigned values, wherein providing the combination comprises, ordering, the plurality of interventions based of a variety of criteria including at least a difficulty of adaption criterion.

9. The method of claim 8, wherein classifying the malady to at least the intervention category further comprises identifying a plurality of predictive interventions as a function of the physiological data and the intervention category.

10. The method of claim 8, wherein assigning efficacy values further comprises determining the efficacy for each combination of the plurality of intervention categories in addressing malady.

11. The method of claim 8, wherein assigning efficacy values further comprises:

training an intervention machine-learning model with training data that includes a plurality of data entries wherein each data entry correlates intervention efficacy to numerical value scales; and assigning efficacy values to the plurality of predictive interventions as a function of the intervention machine-learning model.

12. The method of claim 11, wherein determining efficacy further comprises retrieving the plurality of predictive interventions from each intervention category of the combination and assigning an efficacy value as a function of the intervention classifier.

13. The method of claim 8, wherein assigning values for at least the combination further comprises:

determining a plurality of predictive intervention combinations; and generating an objective function of the plurality of predictive intervention combinations as a function of efficacy in addressing the malady, wherein maximizing the objective function maximizes the efficacy value of the combination.

14. The method of claim 8, wherein providing the predictive intervention further comprises generating an ordering of the plurality of combinations based on efficacy value.

*   *   *   *   *